(12) United States Patent
Lin

(10) Patent No.: US 8,153,166 B2
(45) Date of Patent: Apr. 10, 2012

(54) COMPOSITION FOR PROPHYLAXIS OR TREATMENT OF URINARY SYSTEM INFECTION AND METHOD THEREOF

(76) Inventor: Chih-Hsiung Lin, Taichung (TW)

( * ) Notice: Subject to any disclaimer, the term of this patent is extended or adjusted under 35 U.S.C. 154(b) by 54 days.

(21) Appl. No.: 11/422,924

(22) Filed: Jun. 8, 2006

(65) Prior Publication Data

US 2008/0124405 A1    May 29, 2008

(51) Int. Cl.
*A01N 65/00* (2009.01)
(52) U.S. Cl. .................................................. 424/725
(58) Field of Classification Search .................. None
See application file for complete search history.

(56) References Cited

U.S. PATENT DOCUMENTS

2003/0108629 A1 * 6/2003 Chou ........................... 424/765

FOREIGN PATENT DOCUMENTS

| DE | EP07011162 | | 9/2007 |
| DE | EP07011162 | | 12/2007 |
| DE | EP07011162 | | 8/2008 |
| JP | 2003342179 | | 12/2003 |
| JP | 2005008539 | | 1/2005 |
| KR | 2003-0011731 | | 2/2003 |
| KR | 2003011731 | * | 2/2003 |
| KR | 2003075396 | | 9/2003 |
| TW | 09720122490 | | 3/2008 |
| WO | WO 00/74697 | * | 12/2000 |

OTHER PUBLICATIONS

Mayo Clinic, 9 pages, 2009.*
IBIDS, 2 pages, 2004.*
Science direct, 15 pages, 2004.*
Lance Free star, 3 pages, 2008.*
Beerepoot, MA, et al., Non-antibiotic prophylaxis for recurrent urinary-tract infections, Ned Tijdschr Geneeskd, Mar. 11, 2006, 541-544, 150(10).
Hutchinson, J., et al., Do cranberries help prevent urinary tract infections?, Nurs Times, Nov. 22-28, 2005, 38-40, 101(47).
Cai Y, et al., Astilbin suppresses delayed-type hypersensitivity by inhibiting lymphocyte migration, J Pharm Pharmacol, May 2003, 691-696, 55(5).
Tan, Y., Rouse, J., Zhang, A., Cariati, S., Cohen, P., Comb, M. J. FGF and stress regulate CREB and ATF-1 via a pathway involving p38 MAP kinase and MAPKAP kinase-2. EMBO J. 1996; 15: 4629-4642.
Beyaert, R., Cuenda, A., Vanden, B. W., Plaisance, S., Lee, J. C., Haegeman, G., Cohen, P., Fiers, W. The p38/RK mitogen-activated protein kinase pathway regulates interleukin-6 synthesis in response to tumour necrosis factor. EMBO J. 1996; 15: 1914-1923.
Suttles, J., Milhorn, D. M., Miller, R. W., Poe, J. C., Wahl, L. M., Stout, R. D. CD40 signaling of monocyte inflammatory cytokine synthesis through an ERK1/2-dependent pathway. A target of interleukin (IL)-4 and IL-10 anti-inflammatory action. J. Biol. Chem. 1999; 274: 5835-5842.
Leppert, D., Waubant, E., Galardy, R., Bunnett, N. W., Hauser, S. L. T cell gelatinases mediate basement membrane transmigration in vitro. J. Immunol. 1995; 154: 4379-4389.
Mandal p, Kapil A, Goswami k, Das B, Dwivedi SN. Uropathogenic *E. coli* causing urinary tract infection. Indian J Med Res. Dec. 2001; 114: 207-211.
Conboy IM et al., Proc Natl Acad Sci USA 1999; 96: 6324-29.
Anja Siitonen et al, Microbial Pathogenesis, 1993 ; 15: 65-75.
E.I. Weiss et al, Antiviral Research 66 (2005) 9-12.
A. Brauner et al, Journal of Infection (1995) 31, 27-31.
Claude B, Klee et al, J. Biol. Chem. 1998; 273: 13367-13370.
Simon A. Lewis, Am J Physiol Renal Physiol. (2000) 278:F867-F874.
Yu Cai et al., J pharm Pharmacol. May 2003; 55(5):691-696.
Wu HZ et al, Acta Pharmacol Sin Dec. 2004; 25 (12): 1685-1689.
Puupponen-Pimia R, Nohynek L, Alakomi HL, Oksman-Caldentey KM. Bioactive berry compounds—novel tools against human pathogens. Appl Microbiol Biotechnol. 2005. 67: 8-18.
Taiwan Patent Office Preliminary Rejection, Nov. 10, 2008.
Communication from European Patent Office, Aug. 25, 2008.
Effects of chlorogenic acid, an active compound activating calcineurin, purified from *Flos lonicerae* on macrophage, Wu HZ et al., Acta Pharmacologica Sinica Dec. 2004; 25 (12): 1685-1689.
Purification of astilbin and isoastilbin in the extract of smilax glabra rhizome by high-speed counter-current chromatography, Qizhen Du et al., Journal of Chromatography A. 1077 (2005) 98-101.

* cited by examiner

*Primary Examiner* — Michael Meller
(74) *Attorney, Agent, or Firm* — WPAT, P.C.; Anthony King

(57) ABSTRACT

The present invention relates to a composition for prophylaxis or treatment of urinary system infection, comprising a matrix metalloproteinase inhibitor. The present invention also relates to a method for prophylaxis or treatment of urinary system infection, comprising administering to a patient in need of such treatment an effective amount of composition comprising a matrix metalloproteinase inhibitor.

1 Claim, No Drawings

COMPOSITION FOR PROPHYLAXIS OR TREATMENT OF URINARY SYSTEM INFECTION AND METHOD THEREOF

FIELD OF THE INVENTION

The present invention relates to a composition and a method for prophylaxis or treatment of urinary system infection.

BACKGROUND OF THE INVENTION

Urinary System Infection

Urinary System Infection, in particular urinary tract infection, may be defined as the presence of microorganisms in the urinary tract that can not be accounted for by contamination. The organisms have the potential to invade the tissue of urinary tract and adjacent structures. Such infection may be limited to the growth of bacteria in the urine, which frequently may not produce symptoms. Urinary system infection may also present as several syndromes associated with an inflammatory response to microbial invasion and can range from asymptomatic bacteriuria to pyelonephritis with bacteremia or sepsis.

The microbiologic etiology of urinary system infections usually originates from bowel flora of the host. While virtually every organism has been associated with urinary system infections, certain organisms predominate as a result of specific virulence factors. The most common cause of uncomplicated urinary system infections is *Escherichia coli*, which accounts for almost 85% of community-acquired infections. Additional causative organisms in uncomplicated infections include *Staphylococcus saprophyticus, Proteus* sp., *Klebsiella pneumonia, Pseudomonas aeruginosa, Enterococcus* sp., and *Staphylococcus epidermidis*.

In general, organisms gain entry into the urinary tract via three possible routes: the majority is the ascending, and the minority is the descending (hematogenous), and the very rare possibility, however no evidence, is the lymphatic pathway. The urine under normal circumstances is capable of inhibiting and killing microorganisms, the factors thought to be responsible include a low pH, extremes in osmolality, high urea concentration, high organic acid concentration, and in males the prostatic secretions.

Common Remedy for Urinary System Infection

In cases where treatment is needed for urinary system infections, antibiotics are commonly used.

Antibiotics kill (i.e. bacteriacide) or inhibit (i.e. bacteriastatic) the growth of microorganisms by interfering with specific biosynthesis or metabolism pathways inside the susceptible pathogens, thus depriving them of the metabolites essential to their survival.

The induction of resistance to antibiotic is a fate when the antibiotic is frequently and repeated used. It was shown that the susceptibility of *E. coli* to a certain antibiotic is inversely proportional to the time over which that particular antibiotic has historically been in use; this general trend holds despite some minor differences across antibiotics that may reflect their different frequencies of use.

Matrix Metalloproteinase & Cell Migration

Matrix metalloproteinases (MMPs) are a family of zinc- and calcium-dependent endopeptidases, which includes matrilysin, stromelysins, gelatinases, interstitial and neutrophil collagenases, collagenase-3 (MMP-13) and membrane-type MMPs. They digest different components of the extracellular matrix during physiologic and pathologic turnover (Tan, Y., Rouse, J., Zhang, A., Cariati, S., Cohen, P., Comb, M. J. FGF and stress regulate CREB and ATF-1 via a pathway involving p38 MAP kinase and MAPKAP kinase-2. EMBO J. 1996; 15: 4629-4642). The gelatinase-type matrix MMPs, MMP-2 and MMP-9, are capable of degrading type IV collagen in the basement membrane and thus are regarded as key enzymes in migration and invasion by several cell types, including macrophages, T cells and some tumour cells (Beyaert, R., Cuenda, A., Vanden, B. W., Plaisance, S., Lee, J. C., Haegeman, G., Cohen, P., Fiers, W. The p38/RK mitogen-activated protein kinase pathway regulates interleukin-6 synthesis in response to tumour necrosis factor. EMBO J. 1996; 15: 1914-1923; Suttles, J., Milhorn, D. M., Miller, R. W., Poe, J. C., Wahl, L. M., Stout, R. D. CD40 signaling of monocyte inflammatory cytokine synthesis through an ERK1/2-dependent pathway. A target of interleukin (IL)-4 and IL-10 anti-inflammatory action. J. Biol. Chem. 1999; 274: 5835-5842). Recently, constitutive secretion of MMP-9 and activation-induced secretion of MMP-2 have been shown to favour T-cell migration through a basement membrane in-vitro (Leppert, D., Waubant, E., Galardy, R., Bunnett, N. W., Hauser, S. L. T cell gelatinases mediate basement membrane transmigration in vitro. J. Immunol. 1995; 154: 4379-4389). Inhibition of T cell transmigration by interfering with the expression of these proteinases may represent a useful approach to the treatment of T-cell-mediated inflammation and autoimmune diseases.

Medical Uses of Matrix Metalloproteinase Inhibitors

Matrix metalloproteinases have been linked to cancers such as breast, ovarian, colorectal, and lung. Synthetic matrix metalloproteinase inhibitors are being explored for use in cancer prevention and treatment because of their demonstrated antimetastatic and antiangiogenic properties. Matrix metalloproteinase inhibitors include compounds such as: Marimastat (BB-2516), COL-3, BAY 12-9566, and KB-R7785. Marimastat (BB-2516) was the first orally bio-available matrix metalloproteinase inhibitor to enter clinical trials in the field of oncology. Developing nontoxic, orally active, MMP inhibitors is important because these compounds will likely need chronic administration in combination with other therapies. However, MMP inhibitor was never used in terms of urinary system infection.

SUMMARY OF THE INVENTION

The present invention relates to a composition for prophylaxis or treatment of urinary system infection, comprising a matrix metalloproteinase inhibitor. The present invention also relates to a method for prophylaxis or treatment of urinary system infection, comprising administering to a patient in need of such treatment an effective amount of composition comprising a matrix metalloproteinase inhibitor.

DETAILED DESCRIPTION OF THE INVENTION

Mechanism of Urinary System Infection

Once bacteria reach the urinary tract, three factors determine the development of infection: (1) the size of the inoculum and the retention time of the bacteria in the urinary tract, (2) the virulence of the microorganism, and (3) the competency of the natural host defense mechanisms.

An important virulence factor of bacteria is their ability to adhere to urinary epithelial cells, resulting in colonization of the urinary infections, and pyelonephritis. The mechanism of adhesion of G (−) bacteria, particularly *E. coli*, is related to the bacterial fimbriaes which adhere to specific glycolipid components on epithelial cells. The most common type of fimbriae is type 1, which is mannose sensitive (MS fimbriae), can bind to mannose residues present in glycoproteins (e.g. Tamm-Horsfall protein produced by the ascending limb of Henle and distal tubule, which is secreted into the urine and contains mannose residues), or in glycosaminoglycan (i.e. the mucus lining which covers the epithelial cells of the bladder and urinary tract), or in specific glycolipid components on epithelial cells. Other fimbriaes, such as P or F fimbriae (MR fimbriae), are mannose resistant, tend to bind avidly to specific glycolipid receptors on uroepithelial cells and are more frequently associated with recurrent urinary system infection or pyelonephritis (Mandal p, Kapil A, Goswami k, Das B, Dwivedi S N. Uropathogenic *E. coli* causing urinary tract infection. Indian J Med Res. 2001 December; 114: 207-11). Other virulence factors include the production of hemolysin and aerobactin. Hemolysin is a cytotoxic protein produced by bacteria that causes release of inflammatory mediator at lower concentration and lyses a wide range of cells, including erythrocytes, PMNs, and monocytes, at higher concentration.

The normal urinary tract is typically resistant to colonization and infection by pathogenic bacteria. The majority of urinary system infections reflect a failure in host defense mechanisms. There are several known abnormalities of the urinary tract system that interfere with its natural defense mechanisms, the most important of which is obstruction. Obstruction can inhibit the normal flow of urine, disrupting the natural flushing and voiding effect in removing bacteria from the bladder and resulting in incomplete empting, which including prostatic hypertrophy, calculi, tumors, urethral strictures, usage of anticholinergic drugs, and neurologic malfunction associated with stroke, diabetes, spinal cord injuries and other neuropathies etc. Other risk factors include urinary reflux, urinary catheterization, mechanical instruments, pregnancy, and the use of spermicides and diaphragms. The short length of the female urethra and its proximity to the perirectal area also make colonization of the urethra more likely.

In the present invention, the urinary system infection is not limited but to includes urethritis, cystitis, prostatitis, epididymitis, pyelonephritis, asymptomatic bacteriuria, symptomatic urinary system infection, bacteriuria, hematuria, hemuresis, pyuria and urosepsis. In general, the urinary system infection is caused by pathogen comprising one or more organisms selected from the group consisting of *E. coli, Proteus mirabilis, Klebsiella pneumoniae, Pseudomonas aeruginosa, Chlamydia, Mycoplasm, Staphylococcus saprophyticus, Proteus* sp., *Enterococcus* sp., and *Staphylococcus epidermidis*, preferably *E. coli*.

Designation of Composition for Prophylaxis or Treatment of Urinary System Infection The present invention discloses a composition that aims to resolve the above mentioned dilemma of anti-infection and resistance-induction in using antibiotics to treat recurrent urinary system infection.

The designed composition of the invention comprises four categories synergic active ingredients: (i) a pathogen isolator; (ii) a urine pH stabilizer; (iii) matrix metalloproteinase inhibitors and (iv) macrophage function modulators.

A. Matrix Metalloproteinase Inhibitor (MMP inhibitor)

Accordingly, the present invention relates to a composition for prophylaxis or treatment of urinary system infection, comprising a matrix metalloproteinase inhibitor. The matrix metalloproteinase inhibitor is preferably selected from the group consisting of *Zizyphus jujuba, Malva sylvestris, Opuntia Streptacantha, Cinnamomi Cortex, Hippophae rhamnoides, Panax ginseng, Eriobotrya japonica, Citrus depressa Hayata, Nelumbo nucifera, Mosla chinensis, Fructus schisandrae, Dalbergia odorfera, Smilax glabra*, kale and their extracts. In a preferred embodiment, the matrix metalloproteinase inhibitor comprises at least one of the said ingredients.

The MMP inhibitor aims to control the spread of inflammatory response thereby to protect the normal defense function of the lining glycosaminoglycan which covers apical membrane in the urinary bladder and in the urinary tract.

The integrity of the structural proteins (e.g. glycosaminoglycan) plays essential roles for the defense function of urinary tract and gall bladder. When active cells (e.g. macrophage, pathogens, cancer cells, etc.) migrate and invade within extracellular matrix tissues composed of the structural proteins, they produce or induce the production of MMPs to degrade protein-containing structure between cell membranes. Therefore MMP inhibitor is able to control the spread of inflammatory response.

A preferred embodiment of the MMP inhibitor contains several flavonol-glycosides such as astilbin, which inhibits the activity of matrix metalloproteinases (MMPs, MMP-2 and 9). Therefore, the MMP inhibitor can control the spread of inflammatory response of urinary system infection by suppressing cell migration, via down-regulating MMP activity (Yu Cai et al., J pharm Pharmacol. 2003 May; 55(5):691-696); the MMP inhibitor can also inhibit delayed-type hypersensitivity reactions through selectively suppressing the lymphocyte functions.

MMP inhibitors may derive from natural herbs, plants, or botanical foods. Such MMP inhibitors are not limited but from *Zizyphus jujuba, Malva sylvestris, Opuntia Streptacantha, Cinnamomi Cortex, Hippophae rhamnoides, Panax ginseng, Eriobotrya japonica, Citrus depressa Hayata, Nelumbo nucifera, Mosla chinensis, Fructus schisandrae, Dalbergia odorfera, Smilax glabra*, kale and their extracts (JP2005008539, JP2003342179 and KR2003075396).

Preferably, the composition of the invention further comprises at least one component selected from the group consisting of a macrophage function modulator, a pathogen isolator, and a urine pH stabilizer. Each of the said components is described as follows.

B. Macrophage Function Modulator

Recent studies have reported the important effects on macrophages by blocking calcineurin (Conboy I M et al., Proc Natl Acad Sci USA 1999). In addition, extract of Chlorogenic acid could activate calcineurin enzyme and enhance the macrophage functions both in vivo and in vitro (Wu H Z et al, Acta Pharmacol Sin 2004 December; 25 (12): 1685-1689).

Accordingly, proper macrophage function modulator can enhance the host defense mechanism through immunity modulation. In the preferred embodiment, macrophage function modulators are able to activate the activity of calcineurin enzyme.

The macrophage function modulator includes but is not limited to *Lonicera japonica Thunb., Cordeceps sinensis, Sophorae Radix, Hippophae rhamnoides, Flos Lonicerae, Pulsatillae Radix*, extract of the dried leaf of *Camellia sinensis* (L.) *C. Kuntze, Ganoderma lucidum, Gynostemma pentaphyllum, Cynara Scolymus L, Thyme, Fructus Schisandrae, Prunellae spica, Lophatheri spica, Coptis Chinensis Franchet*, Dandelion (*Taraxacum officinale* F. Weber ex Wiggers), *Portulacae Herba, Gardeniae Fructus, Sophora subprostrata Radix, Houttuynia cordata Thum, Forsythia suspense* (Thum) *Vahl, Smilax glabra* and *Coptis groenlandica Salisb*. In a preferred embodiment, the macrophage function modulator comprises at least one of the said ingredients.

Furthermore, matrix metalloproteinase inhibitors and macrophage function modulators further contribute to the anti-infection and anti-inflammation effect of the composition of the invention.

In the composition of the present invention, the ratio of weight percent of the matrix metalloproteinase inhibitor to the macrophage function modulator is between 20:1 and 1:5. The preferred weight ratio of the matrix metalloproteinase inhibitor to the macrophage function modulator is between 2:1 and 1:2.

C. Pathogen Isolator

The composition can also comprise a pathogen isolator. The pathogen isolator aims to bind to the fimbriaes (such as mannose sensitive fimbriae or mannose resistant fimbriae) or other adhesive structures of the pathogens thereby to inhibit the bacterial adhesive activity in the urinary tract. In a preferred embodiment, the pathogen isolator includes ellagitannins, proanthocyanidins or polyphenolics.

Cranberry ingredients can reduce the incidence of bacteriuria and pyuria; in particular, proanthocyanidins have been clarified to inhibit adherence of uropathogenic P-fimbriaed *E. coli*. Complex phenolic polymers, such as ellagitannins, also have been identified as strong antibacterial agents (Puupponen-Pimia R, Nohynek L, Alakomi H L, Oksman-Caldentey K M. Bioactive berry compounds—novel tools against human pathogens. Appl Microbiol Biotechnol. 2005.67:8-18).

Preferably, the pathogen isolator includes but is not limited to cranberry, cloudberry, raspberry, strawberry, bilberry, *Hippophae rhamnoides, Vitis vinifera L., Hibiscus sabdariffa* L., grape seeds etc. and the extract thereof. In a preferred embodiment, the pathogen isolator comprises at least one of the said ingredients.

D. Urine pH Stabilizer

The antibacterial effect in the urinary tract is affected by the pH of urine; therefore, a urine pH stabilizer is needed. The urine pH stabilizer is selected from the group consisting of glycolic acid, gallic acid, ellagic acid, vanillic acid, citric acid, malic acid, tartaric acid, lactic acid, and vitamin C.

A preferred embodiment of the urine pH stabilizer is vitamin C. A low dose of vitamin C in the formula of the composition of the invention is expected to stabilize the pH of urine within the weakly acidic range to optimize the natural antibacterial effect in the urinary tract, but not to irritate the stomach or the bladder.

In general, the majority of urinary system infections reflect a failure in host defense mechanisms. The composition of the invention strengthens the host defense mechanism through four synergic functions: pathogen isolation by extract of cranberry, stabilization of urine pH within the weakly acidic range by vitamin C, control of the spread of inflammatory response through inhibition of active cells migration by MMPs inhibitors, and lastly immunity modulation by macrophage modulators.

The composition of the invention differs from antibiotics in two ways. First, the anti-infection function of the composition of the invention is not mainly directly involved in the pathogen's internal metabolism inhibition; induction of resistance is therefore mainly avoided, or at least remarkably reduced. Second, besides anti-infection effect, the composition of the invention is expected to further exhibit anti-inflammatory effect, which the antibiotics lack. Therefore, the composition of the invention has the potential to be (a) used for prophylaxis treatment of frequently recurrent urinary system infections, (b) complementary to antibiotic treatment and (c) alternative to the first line antibiotic treatment.

Those skilled in the art may reasonably expect that the subjects or patients, to which these compositions are delivered, can be any vertebrate animals, most preferred patients are humans having urinary system infection or at risk of urinary system infection. Nonetheless, the utility of the compositions toward any vertebrate can be determined without undue experimentation by administering the composition comprising MMP inhibitors to a cultured cell specific to the vertebrate in question (Yu Cai et al., J pharm Pharmacol. 2003 May; 55(5):691-696).

The composition comprising MMP inhibitors may be administered to a vertebrate by any suitable route known in the art including, for example, orally, intravenous, subcutaneous, intratumoral, intramuscular, transdermal, intrathecal, intrabladder, intraurethan, intrauterus, or intravagina. Administration can be either rapid as by injection, or over a period of time as by slow infusion or administration of a slow release formulation.

It is contemplated that the compositions comprising MMP inhibitors are usually employed in the form of pharmaceutical preparations. Such preparations are made in a manner well known in the pharmaceutical art. One preferred preparation utilizes a vehicle of physiological saline solution; it is contemplated that other pharmaceutically acceptable carriers such as physiological concentrations of other non-toxic salts or compounds, 5% aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption. Such excipients are those substances usually and customarily employed to formulate dosages for parenteral administration in either unit dosage or multi-dose form or for direct infusion by continuous or periodic infusion.

It is also contemplated that certain formulations comprising the compositions that comprise MMP inhibitors are to be administered orally. Such formulations are preferably formulated with suitable carriers, excipients, lubricants, emulsifying agents, suspending agents, sweetening agents, flavor agents, preserving agents and pressed as tablet or encapsulated as solid capsule or soft capsule. Or it is contemplated that such formulations are designed as following dosage forms, either oral solution, or oral sachet, or oral pellet. Or apart from being administered orally, it is contemplated that such formulations are designed as enema, or suppository, or implant, or patch, or cream, or ointment dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic, nucleic acid and other degradation and/or substances that promote absorption such as, for example, surface active agents.

The compositions comprising MMP inhibitors are administered to vertebrates in a pharmaceutically effective amount. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

Method for Prophylaxis or Treatment of Urinary System Infection

The present invention further relates to a method for prophylaxis or treatment of urinary system infection, comprising administering to a patient in need of such treatment an effective amount of said composition in the foregoing descriptions, which comprises a matrix metalloproteinase inhibitor. Such matrix metalloproteinase inhibitor is not limited but from *Zizyphus jujuba, Malva sylvestris, Opuntia Streptacantha, Cinnamomi Cortex, Hippophae rhamnoides, Panax ginseng, Eriobotrya japonica, Citrus depressa Hayata, Nelumbo nucifera, Mosla chinensis, Fructus schisandrae, Dalbergia odorfera, Smilax glabra*, kale and their extracts. Preferably, the matrix metalloproteinase inhibitor is an inhibitor of MMP-2 and/or MMP-9.

Preferably, said composition for the method further comprises at least one component selected from the group consisting of a macrophage function modulator, a pathogen isolator, and a urine pH stabilizer.

Among them, the macrophage function modulator is able to activate the activity of calcineurin enzyme and is not limited but from *Lonicera japonica Thunb., Cordeceps sinensis, Sophorae Radix, Hippophae rhamnoides, Flos Lonicerae, Pulsatillae Radix*, extract of the dried leaf of *Camellia sinensis* (L.) C. *Kuntze, Ganoderma lucidum, Gynostemma pentaphyllum, Cynara Scolymus L, Thyme, Fructus Schisandrae, Prunellae spica, Lophatheri spica, Coptis Chinensis Franchet, Dandelion (Taraxacum officinale* F. Weber ex Wiggers), *Portulacae Herba, Gardeniae Fructus, Sophora subprostrata Radix, Houttuynia cordata Thum, Forsythia suspense (Thum) Vahl, Smilax glabra* and *Coptis groenlandica Salisb.*

The pathogen isolator aims to bind to the fimbriaes (such as mannose sensitive fimbriae or mannose resistant fimbriae) or other adhesive structures of the pathogens thereby to inhibit the bacterial adhesive activity in the urinary tract. In a preferred embodiment, the pathogen isolator includes ellagitannins, proanthocyanidins or polyphenolics. In a preferred embodiment, the pathogen isolator is selected from the group consisting of cranberry, cloudberry, raspberry, strawberry, *Hippophae rhamnoides, Vitis vinifera L., Hibiscus sabdariffa* L., grape seeds and the extract thereof. In the most preferred embodiment, the pathogen isolator is cranberry.

A urine pH stabilizer may have antibacterial effect in the urinary tract by stabilizing the pH of urine. Such urine pH stabilizer is not limited but from glycolic acid, gallic acid, ellagic acid, vanillic acid, citric acid, malic acid, tartaric acid, lactic acid, and vitamin C, preferably vitamin C.

Those skilled in the art may reasonably expect that the subjects or patients, to which these methods are directed, can be any vertebrate animals, most preferred patients are humans having urinary system infection or at risk of urinary system infection. Nonetheless, the utility of the methods toward any vertebrate can be determined without undue experimentation by administering the composition comprising MMP inhibitors to a cultured cell specific to the vertebrate in question (Yu Cai et al., J pharm Pharmacol. 2003 May; 55(5):691-696).

The administration of the composition comprising MMP inhibitors to a vertebrate may be carried out via any suitable route known in the art including, for example, orally, intravenous, subcutaneous, intratumoral, intramuscular, transdermal, intrathecal, intrabladder, intraurethan, intrauterus, or intravagina. Administration can be either rapid as by injection, or over a period of time as by slow infusion or administration of a slow release formulation.

It is also contemplated that certain formulations comprising the compositions that comprise MMP inhibitors are to be administered orally. Such formulations are preferably formulated with suitable carriers, excipients, lubricants, emulsifying agents, suspending agents, sweetening agents, flavor agents, preserving agents and pressed as tablet or encapsulated as solid capsule or soft capsule. Or it is contemplated that such formulations are designed as following dosage forms, either oral solution, or oral sachet, or oral pellet. Or apart from being administered orally, it is contemplated that such formulations are designed as enema, or suppository, or implant, or patch, or cream, or ointment dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic, nucleic acid and other degradation and/or substances that promote absorption such as, for example, surface active agents.

In the invention, the compositions comprising MMP inhibitors are administered to vertebrates in a pharmaceutically effective amount. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

EXAMPLES

The examples below are non-limiting and are merely representative of various aspects and features of the present invention.

Example 1

Preparation of Composition of the Invention (I)

To provide the composition for prophylaxis or treatment of urinary system infection, the active component was formulated with suitable pharmaceutically acceptable excipients such as lactose, sorbitol, mannitol, magnesium stearate, and the like. The active component was:

Astilbin Extract: 130 mg/tablet or sachet bag.

The above formulation was processed into tablets or sachet bags with commercial machine.

Example 2

Preparation of Composition of the Invention (II)

To provide the composition for prophylaxis or treatment of urinary system infection, the active components were formulated with suitable pharmaceutically acceptable excipients such as lactose, sorbitol, mannitol, magnesium stearate, and the like. The active components were:

Astilbin Extract: 130 mg/tablet or sachet bag, and
Chlorogenic acid Extract: 60 mg/tablet or sachet bag The above formulation was processed into tablets or sachet bags with commercial machine.

Example 3

Preparation of Composition of the Invention (III)

To provide the composition for prophylaxis or treatment of urinary system infection, the active components were formulated with suitable pharmaceutically acceptable excipients such as lactose, sorbitol, mannitol, magnesium stearate, and the like. The active components were:

Cranberry extract: 150 mg/tablet or sachet bag,
Vitamin C: 70 mg/tablet or sachet bag,
Astilbin Extract: 130 mg/tablet or sachet bag, and
Chlorogenic acid Extract: 60 mg/tablet or sachet bag.

The above formulation was processed into tablets or sachet bags with commercial machine.

Example 4

Efficacy of the Present Composition on Treatment of Urethritis, Cystitis with Hemuresis A 44-year old female nurse was suffering from hemuresis and felt burning pain while urination. Symptoms of Urinary Tract Infection were obvious, e.g. pressure in the lower pelvis, the need of frequent and urgent urination etc. She was a diagnosed recurrent UTI patient by urologist. Before taking medical examination in laboratory, she took twice of the composition of Example 3 within the first 5 hours. Another 2 hours later, symptoms of Urinary Tract Infection alleviate dramatically Instead of visiting the clinic, she then continued to take the Example 3 composition for full 3 days, all symptoms of UTI disappeared.

Example 5

Efficacy of the Present Composition on Treatment of Cystitis which was Resistant to Previous Treatment with the First Line Cephalosporin Antibiotic and Sulfa Drug A menopausal woman was diagnosed with UTI by urologist, urine analysis and culture were also confirmed with high WBC count and two different pathogens. After one week of the first line Cephalosporin antibiotic treatment, WBC count remains positive, and then the antibiotic was replaced with a Sulfa drug for another week, WBC count remains positive again.

This patient was then recommended to take the Example 3 composition, by 3 doses a day, for another one full week. All symptoms of UTI disappeared and the WBC count was clear.

Example 6

Efficacy of the Present Composition on Treatment of Cystitis with Hemuresis and Pyuria A 79-year old stroke woman was unconscious and was on N-G tube and on Foley. She had been suffered from repeated UTI and continuous fever for a while. The urine was cloudy with strong odor and the Foley was precipitated with lots of crystal because of hemuresis and pyuria. After one week of treatment with the Example 3 composition, by 3 doses a day, the urine and the Foley became far clear than before, and the strong odor disappeared, and no more fever.

One skilled in the art readily appreciates that the present invention is well adapted to carry out the objects and obtain the ends and advantages mentioned, as well as those inherent therein. The formulations, processes and methods for producing them, group of patients, administration regiment and dosage plans are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method for treating urethritis or cystitis consisting essentially of administering to a patient in need thereof a therapeutically effective amount of smilax glabra rhizome extracted astilibin and *Flos Lonicerae* extracted chlorogenic acid.

* * * * *